(12) United States Patent
Johnson et al.

(10) Patent No.: US 6,231,509 B1
(45) Date of Patent: *May 15, 2001

(54) APPARATUS AND METHOD FOR MONITORING INTRACRANIAL PRESSURE

(76) Inventors: Royce Johnson, 114 Rimdale, Universal City, TX (US) 78148; William H. Quirk, IV, 508 Garraty, San Antonio, TX (US) 78209

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/206,203

(22) Filed: Dec. 5, 1998

Related U.S. Application Data

(60) Provisional application No. 60/069,195, filed on Dec. 5, 1997.

(51) Int. Cl.[7] ............................................. A61B 8/00
(52) U.S. Cl. ................................. 600/438; 600/451
(58) Field of Search ............................ 600/437, 438, 600/451, 561

(56) References Cited

U.S. PATENT DOCUMENTS

| | | |
|---|---|---|
| 4,363,242 | 12/1982 | Heyman . |
| 5,214,955 | 6/1993 | Yost et al. . |
| 5,388,583 * | 2/1995 | Ragauskas et al. ............. 600/451 |
| 5,404,743 | 4/1995 | Froggatt . |
| 5,617,873 | 4/1997 | Yost et al. . |
| 5,951,476 * | 9/1999 | Beach .............................. 600/437 |
| 5,951,477 * | 9/1999 | Ragauskas et al. ............. 600/437 |

OTHER PUBLICATIONS

McElhaney, James H., "Mechanical Properties of Cranial Bone", J. Biomechanics, vol. 3, pp. 495–511.

Hubbard, Robert P., "Flexure of Layered Cranial Bone", J. Biomechanics, vol. 4, pp. 251–263, Pergamon Press, 1971.

Posnick, Jeffrey C., "Indirect Intracranial Volume Measurement Using CT Scans: Clinical Applications for Craniosynostosis", Craniofacial Program, vol. 89, No. 1, Feb. 1991.

(List continued on next page.)

*Primary Examiner*—Marvin M. Lateef
*Assistant Examiner*—Ali M. Imam

(57) ABSTRACT

An apparatus and a method that permit the accurate measurement and continuous monitoring of the intracranial pressure of humans and vertebrates that eliminates the requirement of direct contact with the patient's head, obviates problems previously encountered with the "soft" interface between transducers and the patient, and minimizes patient discomfort during the measurement process. The apparatus includes a pair of diametrically opposed acoustic transducers controlled and monitored through a switching device by a constant frequency pulsed phase-locked loop signal generator/analyzer. The transducers provided signal data that permits a discrimination of cranial vault width using appropriate signal processing devices. Digital logic devices or microprocessor based devices permit the identification of changes in cranial vault width from which intracranial pressure changes are determined. The method includes transmitting incrementally offset (in time) interrogating acoustic signals from the transducers and receiving reflected signals that include indications of the interior distance between the cranial vault walls. Repeated transmissions and receptions permit a comparison of cranial vault signal transit times and the identification of changes in the cranial vault width. Such changes are correlated with intracranial pressure changes after reference to an initial measured pressure.

2 Claims, 5 Drawing Sheets

OTHER PUBLICATIONS

Krabbel, Gerald, "Development of a Finite Element Model of the Head Using the Visible Human data", The Visible Human Project Conference, National Institutes of Health, Oct. 1996.

B.–Flick, B., "Study and Development of a Portable Telemetric Intracranial Pressure Measurement Unit", Proceedings –19th International Conference –IEE/EMBS Oct. 1997, Chicago, IL.

Simonov LG, Saribekian AS, "Features of volume and pressure pulsations during changes in ' reserve space' within the cranial cavity", Kosm Biol Aviakosm Med, 1997 Jan–Feb. 21:1 61–6.

Herring SW, et al., "Patterns of bone strain in the zygomatic arch", Anat Rec 1996, Dec. 246:4 446–57.

Walsh P, Logan WJ, "Continuous and intermittent measurement of intracranial pressure by Ladd monitor", J Pediatr, 1983 Mar. 102:3 439–42.

Strassburg HM, et al., "Noninvasive intracranial pressure measurement at the anterior fontanelle in the first days of life", Monatsschr Kinderheilkd, 1984 Dec. 132:12 904–8.

Mehta BV, et al., "Comparison of image processing techniques (magnetic resonance imaging, computed tomography scan and ultrasound) for 3D modeling and analysis of the human bones", J. Digit Imaging, 1997 Aug. 10:3 Suppl 1 203–6.

Ivan LP, et al., "Clinical and experimental observations with fontanel pressure measurements", Childs Brain, 1983, 10:6 361–8.

Walsh P, et al., Continuous and intermittent measurement of intracranial pressure by Ladd monitor, J Pediatr, 1983 Mar. 102–103 439–42.

Lacey L., et al., "Effect of application pressure and gestational age on transfontanel pressure in healthy neonatest", Biol Neonate, 1986, 50:3 135–140.

Myerberg DZ, et al., "Comparison of noninvasive and direct measurements of intracranial pressure", Pediatrics, 1980 Mar. 65:3 473–6.

Kaiser G., et al., "Simultaneous measurement of ventricular fluid and fontanelle pressure in neonates and infants with hydrocephalus", Z Kinderchir, 1985 Feb., 4:1 3–6.

* cited by examiner

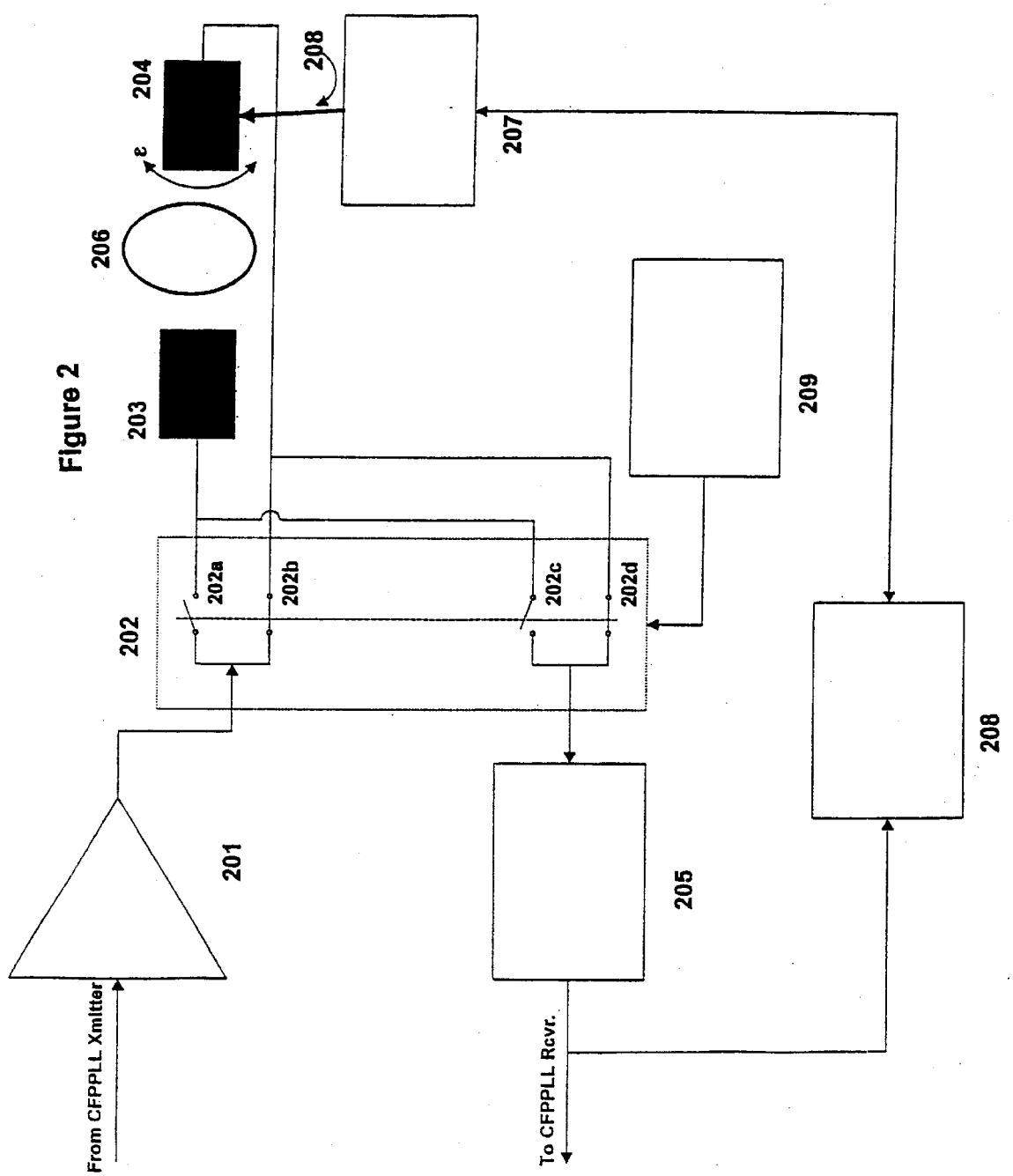

APPARATUS AND METHOD FOR MONITORING INTRACRANIAL PRESSURE

CROSS REFERENCE TO RELATED APPLICATIONS

This application claims the benefit of U.S. Provisional Application No. 60/069,195, filed Dec. 5, 1997.

BACKGROUND OF THE INVENTION

1. Field of the Invention

This invention relates generally to measuring and monitoring intracranial pressure in humans or other vertebrates. In particular, this invention is an apparatus and method which can accurately determine over a period of time, without invasion of the body, whether a subject is experiencing elevated pressure in the cranial vault for the purpose of diagnosing instances of subdural hematoma or other life-threatening conditions.

2. Description of the Related Art

Monitoring of intracranial pressure is of significant diagnostic and post-operative importance for patients with cranial injuries, pathologies, or other conditions, that may affect the pressure of the subarachnoidal fluid around the brain, and for patients who have undergone brain surgery.

Intracranial pressure is regularly measured and monitored by means of a pressure sensor inserted through the skull into the brain. Usually a hole is drilled in the skull, and a catheter with a pressure sensor is inserted into the brain fluid. To obtain a pressure volume index, the change in intracranial pressure is monitored after a known bolus of saline solution is inserted at a known rate. This known procedure, while simple and accurate, is not suitable for long term monitoring, because an open wound must be maintained in the skull for the catheter with the pressure sensor. Antibiotics are only partially effective in treating cranial infections, so the pressure sensor can only be left in situ for two weeks or less.

Long term monitoring of intracranial pressure, without the need for maintaining a open wound in the skull, is possible if a pressure sensor with a transmitter is implanted in the brain. The intracranial pressure is thereafter monitored by means of a receiver located outside the skull. Such a solution is, however, unattractive because of risks involved in implanting anything in the brain, and because of the problems of providing power to a transmitter implant. One such remote pressure sensor is described in U.S. Pat. No. 4,124,023 to Fleischmann et al. However, this device uses nuclear material as an energy source, making it poorly suited for implantation into a human brain.

Other methods, claiming to be non-invasive, are based on the measurement of some quantity that depends on intracranial pressure, but which does not have a fixed relationship to intracranial pressure.

One such method is described in U.S. Pat. No. 4,204,547 to Allocca. Allocca occludes the blood flow in a jugular vein for a few seconds, and measures the resulting rate of change of blood flow within the jugular vein upstream of the occlusion as an indicator of the intracranial pressure.

Another method, as proposed in U.S. Pat. No. 4,564,022 to Rosenfeld et al., directs a sensory stimulus towards the patient, e.g. a flash of light into the eyes, and measures the latency of a negative-going wave of the electrical brain activity as an indicator of intracranial pressure.

These known indirect methods may be used, under very restricted conditions, as possible indicators of variations of the intracranial pressure in a patient. However, values for the intracranial pressure cannot be monitored over an extended period of time without using invasive monitoring methods. Such monitoring is possible by inserting a pressure transducer into the brain of the patient being monitored. This is, however, a traumatic and undesirable procedure.

Recent research suggests that ultrasound can be used to monitor the intracranial pressure in a patient on a continuing basis by using a single ultrasonic transducer aimed at the patient's head to emit a pulse of acoustic energy, part of which propagates through the cranial vault and is reflected by the bone structure on the other side. Thus measurement of the transit time through the intervening matter contained in the cranial vault can be accurately measured by measuring the time between the generation of the ultrasonic pulse to the return of the reflected wavefront.

An apparatus which can accomplish the measurement described is disclosed as the CONSTANT FREQUENCY PULSED PHASE-LOCKED LOOP MEASURING DEVICE in U.S. Pat. No. 5,214,955 (the '955 Patent) to Yost et al., which is herein incorporated by reference. One of the shortcomings of application of the Yost '955 system to the long term monitoring of intracranial pressure is that of the "soft" interface between the face of the transducer and the skull of the target patient. The flesh covering the skull is literally soft, and the transducer's interface with the patient's surrounding skin may vary. Near-field reflections from this interface and the underlying interface between the scalp and the skull can cause erroneous results in the measurement of intracranial pressure unless extreme measures are taken to ensure consistent placement of the measurement transducer. Even if adequate transducer placement precautions are taken, certain other conditions such as the edema which frequently accompanies severe head injuries can exacerbate the problems of accurate placement of the measurement transducer.

SUMMARY OF THE INVENTION

Accordingly, it is the object of the present invention to provide a method for monitoring changes in intracranial pressure over an extended time period without the need for insertion of any pressure sensing apparatus inside the cranial vault.

It is another object of the present invention to provide a method of compensating for certain errors induced by the near-field reflections and other transducer placement factors which adversely effect the accuracy of the values of intracranial pressure measurements.

This invention concerns an apparatus and a method of using same which enables the accurate measurement and continuous monitoring of intracranial pressure, so that over time accurate repeatable measurements can be taken without undue burden being placed on the personnel making the measurements, and more importantly, minimizing patient discomfort due to prolonged setup time for the measurements.

Instead of using a single transducer to measure the transit time of sound through the cerebrospinal fluid and other intervening matter in the cranial vault, an additional transducer is employed which is diametrically opposed to the first transducer. In this manner, as will become apparent to those skilled in the art, the requirement for direct contact with the patient's head is eliminated, which obviates the problem of the "soft" interface described above, and also minimizes patient discomfort during the measurement process.

BRIEF DESCRIPTION OF THE DRAWINGS

FIG. 2 is a schematic view showing the control circuitry of a preferred embodiment in relation to patient (206) and a constant frequency pulsed phase-locked loop measuring system.

DETAILED DESCRIPTION OF PREFERRED EMBODIMENTS

Figure 1A:
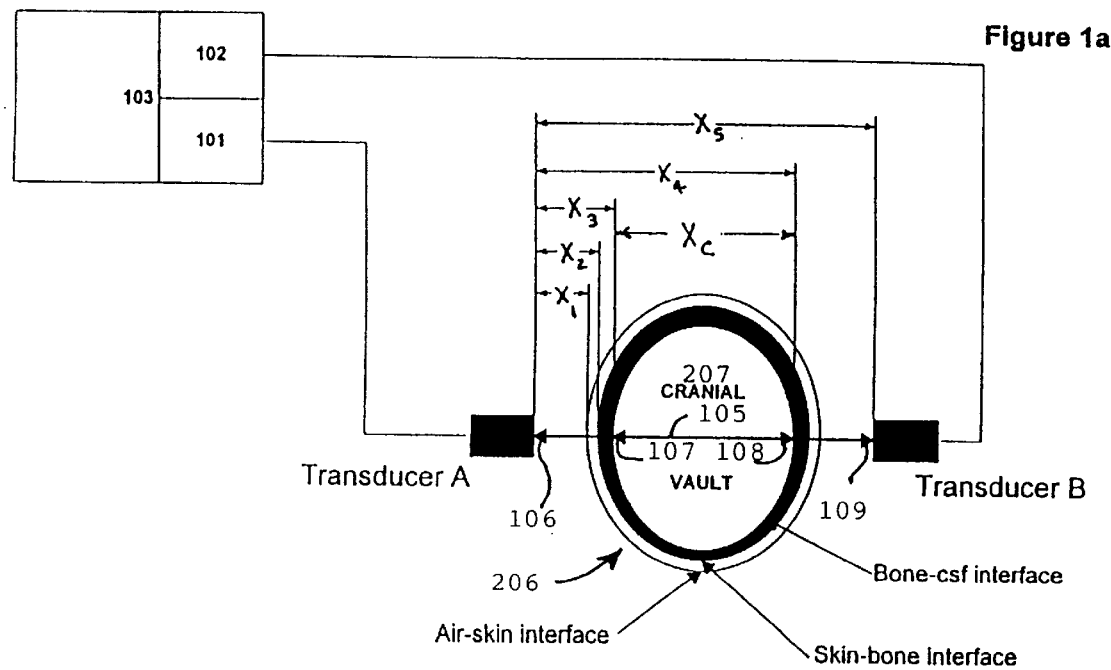
FIG. 1a is a schematic view of a preferred embodiment of the present invention, with transducers A and B operatively positioned for measuring the intra-cranial pressure (ICP) of a patient (206).
Figure 1B:
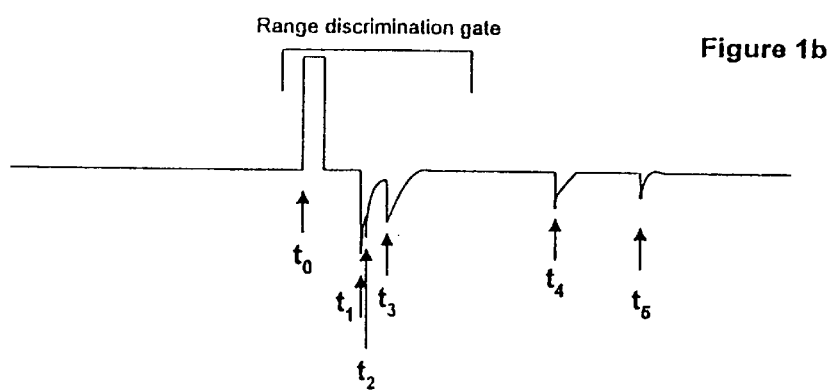
FIG. 1b is a simplified timing graph illustrating reflected acoustic energy as it might appear on an oscilloscope after firing one of the transducers (A or B) of FIG. 1a at time $t_0$.

Referring to FIGS. 1a and 1b, an apparatus according to a preferred embodiment is shown. A constant frequency pulsed phase-locked loop (CFPPLL) measuring device (103), similar to the one described in the '955 Patent, is shown as electrically connected through novel switching apparatus, (101) and (102) (to be discussed later), to acoustic transducers A and B like those described in the '955 Patent.

In the operation of one embodiment of the present invention, either transducer A or transducer B is selected through switching apparatus (101) or (102) to be "fired." A transducer is "fired" by supplying a pulsed burst of electrical energy from the CFPPLL measuring device (103). When a transducer (A or B) is fired, it transmits acoustic energy. Ideally, such acoustic energy is transmitted in a given direction which, if transducers A and B are oriented properly, is toward the other one of transducers A and B. Acoustic energy is represented in FIG. 1a by the thick double-arrow connectors (105) between transducers A and B. The arrowheads (106–109) of connectors (105) illustrate some of the locations ("reflection points") where the acoustic energy is reflected. The target patient (206) is positioned between the two transducers A and B so that the acoustic energy passes through the cranial vault (207) of patient (206). The patient's cranial vault (207) is shown in cross section from a top view in FIG. 1a.

In its path (105) through the target cranial vault (207) the acoustic energy encounters several significant boundary layers where the medium of acoustic transmission changes. A reflection of some of the acoustic energy occurs at each such boundary layer, the magnitude of the reflection being dependent upon the density of the medium encountered with respect to the medium from which the energy is entering. These principles are well known to those versed in the art of acoustic measurements, and will not be discussed in detail here.

Assuming transducer A is fired at time $t_0$, FIG. 1b shows a simplified timing graph of the returned reflections as they might appear on an oscilloscope. The "main bang" or firing pulse is the large positive-going pulse at $t_0$. After the energy travels a distance of $x_1$, as shown in FIG. 1a, an air-to-skin boundary layer (labeled "air-skin interface" in FIG. 1a) is encountered and some of the acoustic energy is reflected. The reflected pulse observed at transducer A is depicted as the negative energy spike (or "event") occurring at time $t_1$. After passing the air-to-skin boundary layer, the acoustic energy travels through the scalp and encounters the outer surface of the skull, located at distance $x_2$, causing another boundary-layer reflection depicted as the event at time $t_2$ in FIG. 1b. After traveling through the skull, the acoustic energy encounters the boundary layer of the skull and the subarachnoidal fluid surrounding the brain. This causes the reflection depicted as the event at time $t_3$ in FIG. 1b. No other major reflective events occur until the boundary layer is encountered between the subarachnoidal fluid and the other side of the skull at a distance $x_4$, depicted as the event at time $t_4$ in FIG. 1b. Similar reflections occur as the energy travels through the layers of bone and skin on the other side of the target patient's head, but these can be ignored, as they are so far attenuated by the return journey and resultant reflections as to be negligible. Also, as will be seen from the discussion of the present invention, these reflections are of no consequence in obtaining the measurements of interest. Since there is such a difference between the density of air and the face of the transducers, however, the reflection from the face of transducer B located at a distance $x_5$ can be seen and is of consequence in the discussion of the present invention. This transducer reflection is depicted as the event at time $t_5$ in FIG. 1b.

A major problem in obtaining repeatable measurements of the propagation time of the acoustic pulse through the cranial vault using methods proposed in previous studies becomes evident when one examines the timing chart depicted in FIG. 1b. When a single transducer is utilized, as has been done in the past, the cluttered near-field temporal region from $t_1$–$t_3$ makes it very difficult to determine the point from which to begin counting the transit time across the cranial vault (207). Known signal processing techniques which measure temporal events require a stable point at which to commence the count and a stable point at which to terminate the count. Due to the multiplicity of possible trigger events, and variation of parameters such as the thickness of the scalp and skull bone layers, a stable and dependable trigger point is extremely difficult to attain.

In order to solve this problem, the present invention utilizes a second transducer, depicted as transducer B in FIG. 1a. One embodiment of the apparatus which accomplishes repeatable and accurate measurement of the acoustic propagation properties of the matter within the cranial vault, which is known to reliably correlate to the intracranial pressure is shown schematically in FIG. 2. For the following discussion, the embodiment of FIG. 2 is connected to a CFPPLL measuring device similar to the one described in the '955 Patent, particularly according to the embodiment depicted in FIG. 3 of the '955 Patent.

The special interface circuitry referred to as elements (101) and (102) in FIG. 1a is shown in FIG. 2 united as the switch element (202), consisting of individual switch elements (202 a–d). More particularly, elements (101) and (102) of FIG. 1a are shown as elements (202 a–b) and (202 c–d), respectively, in FIG. 2. These switch elements (202 a–d) control which transducer is to be connected to the amplifier (201), which corresponds to the amplifier (20) of the '955 Patent FIG. 3. Switch element (202) ensures that the two transducers A and B (also designated (203) and (204)) are never fired simultaneously at the skull of the target patient (206). They also control which transducer is connected to the receiver of the '955 Patent's CFPPLL. The control of switch (202) is accomplished by switch control unit (209). The operation of the switch of the switch (202) can be accomplished by a connection to the logic and timing unit of the '955 Patent's CFPPLL device by use of discrete logic elements which are known in the art, or a microprocessor (not shown).

Figure 3:
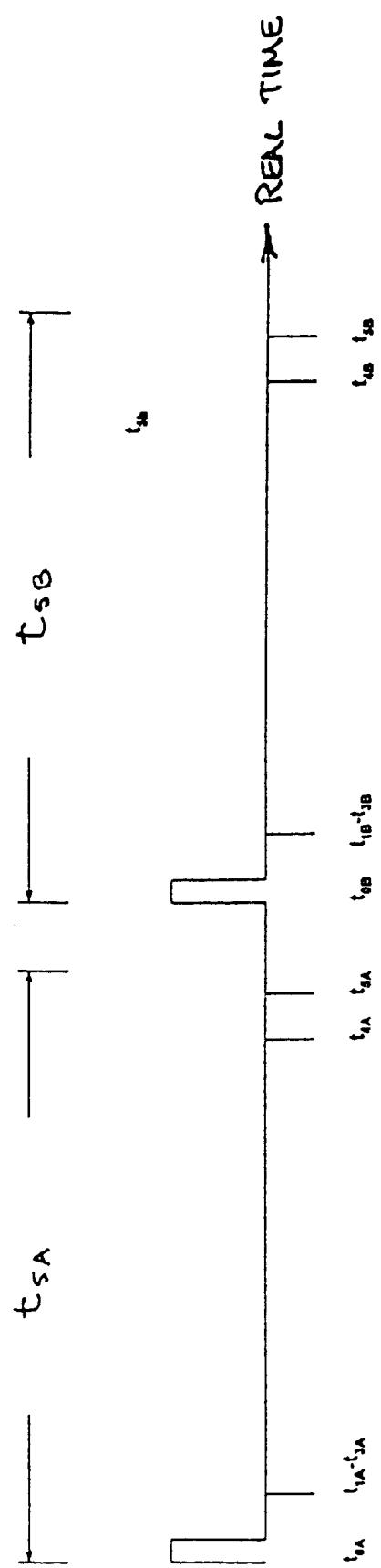
FIG. 3 is an event timeline showing a typical firing sequence for transducers A and B or (203) and (204).

The exact timing of the firing of transducers (203) and (204) is not especially critical, as long as they are fired at roughly the same time but not simultaneously. Preferably, the two transducers (203) and (204) are fired close enough in time to exclude time-dependent pressure variations such as caused by the periodic beating of the heart. On the other hand, the two transducers (203) and (204) should be fired far enough apart in time to allow acoustic reflections to be distinguished from the acoustic energy transmitted from the opposite transducer. Most preferably, the last-fired transducer (203) or (204) is fired within one millisecond after the time $t_5$ of the previously-fired transducer. A more simultaneous alternative method fires the second transducer at approximately half the time $t_5$ of the previously-fired transducer. A typical firing sequence is depicted in FIG. 3, with transducer A or (203) fired first (at time $t_{0A}$) and transducer B or (204) fired second (at time $t_{0B}$). The time between $t_{5A}$ and $t_{0B}$ in FIG. 3 typically does not exceed about one millisecond.

The range discrimination gate period depicted in FIG. 1b is generated by the gate of the '955 Patent's FIG. 3 element (numbered 26) in cooperation with the timing and logic element (numbered 14) of that FIG. 3. This gate apparatus is depicted schematically as element (205) in FIG. 2 in this present specification. The generation of such control signals is known in the art and can be accomplished as described in the '955 Patent. The range discrimination gate is preferably adjusted such that the receiver of the CFPPLL is not responsive to any signal significantly prior to time $t_4$. Thus, the first event which passes to the time measurement process of CFPPLL is the event observed at time $t_4$. In this manner, the time $t_{4A}$ is measured, and immediately thereafter the time $t_{5A}$ is obtained. During the next transducer acquisition frame (i.e., corresponding to transducer B), events $t_{4B}$ and $t_{5B}$ are similarly obtained. Knowing that $T_{5A}$ and $t_{5B}$ should be virtually the same because they both correspond to the distance between transducers A and B, this information (i.e., $T_{4A}$, $t_{5A}$, $t_{4B}$ and $T_{5B}$) is then processed to determine the width of the cranial vault (207).

The first objective of the method of the invention is to use the timing of acoustic reflections to obtain an indication of the width of the cranial vault (207) (i.e., the distance $x_C$ between arrow-heads (107) and (108) in FIG. 1a. As illustrated in FIG. 1b, this width $x_c$ is $x_4$ minus $x_3$. Accordingly, the difference between the times $t_4$ and $t_3$ will be indicative of the width $x_c$ of the cranial vault (207). The time which corresponds to a reflection over the distance from $x_4$ in FIG. 1a to the face of transducer B (i.e., $x_5$) is $T_{5A}-T_{4A}$. Likewise, the time which corresponds to a reflection over the distance $x_3$ in FIG. 1a is $T_{5B}-T_{4B}$. Under normal operating conditions, since events $T_{5A}$ and $T_{5B}$ are equal in magnitude, they will cancel out of the equation. Because $x_3$ is difficult to obtain from a single transducer, $x_3$ is derived from the opposite transducer. In other words using the A–B subscripts, the width of the cranial vault (207) could also be reflected as:

$$x_C = x_{4A} - x_{3A}$$
$$= x_{4A} - (x_{5B} - x_{4B})$$
$$= x_{4A} + x_{4B} - x_{5B}$$

Likewise, where $t_c$ would correspond to an acoustic reflection over $x_c$:

$t_c = T_{4A} + t_{4B} - (t_{5B}$ or $T_{5A}$ or an average thereof)

Hence, because a patient's ICP is related to the width of his/her cranial vault, and since $t_{4A}$, $t_{4B}$ and $t_{5A/B}$ can be reliably measured using the present invention, a repeatable and stable indicator of intracranial pressure can be derived and monitored non-invasively with the present invention. Changes in $t_c$ can be monitored as an indicator of changes in a patient's ICP. Moreover, assuming given values of $t_c$ can be accurately correlated (or calibrated) with known values of a patient's ICP (using either invasive or non-invasive techniques), then the patient's ICP can later be approximated based on changes in $t_c$ using known extrapolation techniques.

In order to ensure that the measurements obtained by the apparatus of the present invention are reliable, the two transducers A and B of FIG. 1a must be coaxially aligned so that the events at $T_{5A}$ and $T_{5B}$ can be accurately and repeatable measured. One embodiment which accomplishes this is illustrated in FIG. 2, where an alignment servo drive (210) receives the output of a servo controller (208). The output of the servo controller (208) is proportional to the angular error g shown in FIG. 2. Although only one servo axis is shown in FIG. 2, it will be understood to those skilled in the art that another axis of control which is orthogonal to the plane in which g lies, i.e. coming out of the plane of FIG. 2, is required in order to accurately align the transducers. The actual alignment can be accomplished manually by an operator observing the signal strength of the $T_{5A}$ events, or can be accomplished by a mechanical angular drive link shown schematically as the path (212) in FIG. 2. The operator will know that the transducers are substantially aligned when the signal strength of the $t_{5A}$ events is greatest.

Figure 4:
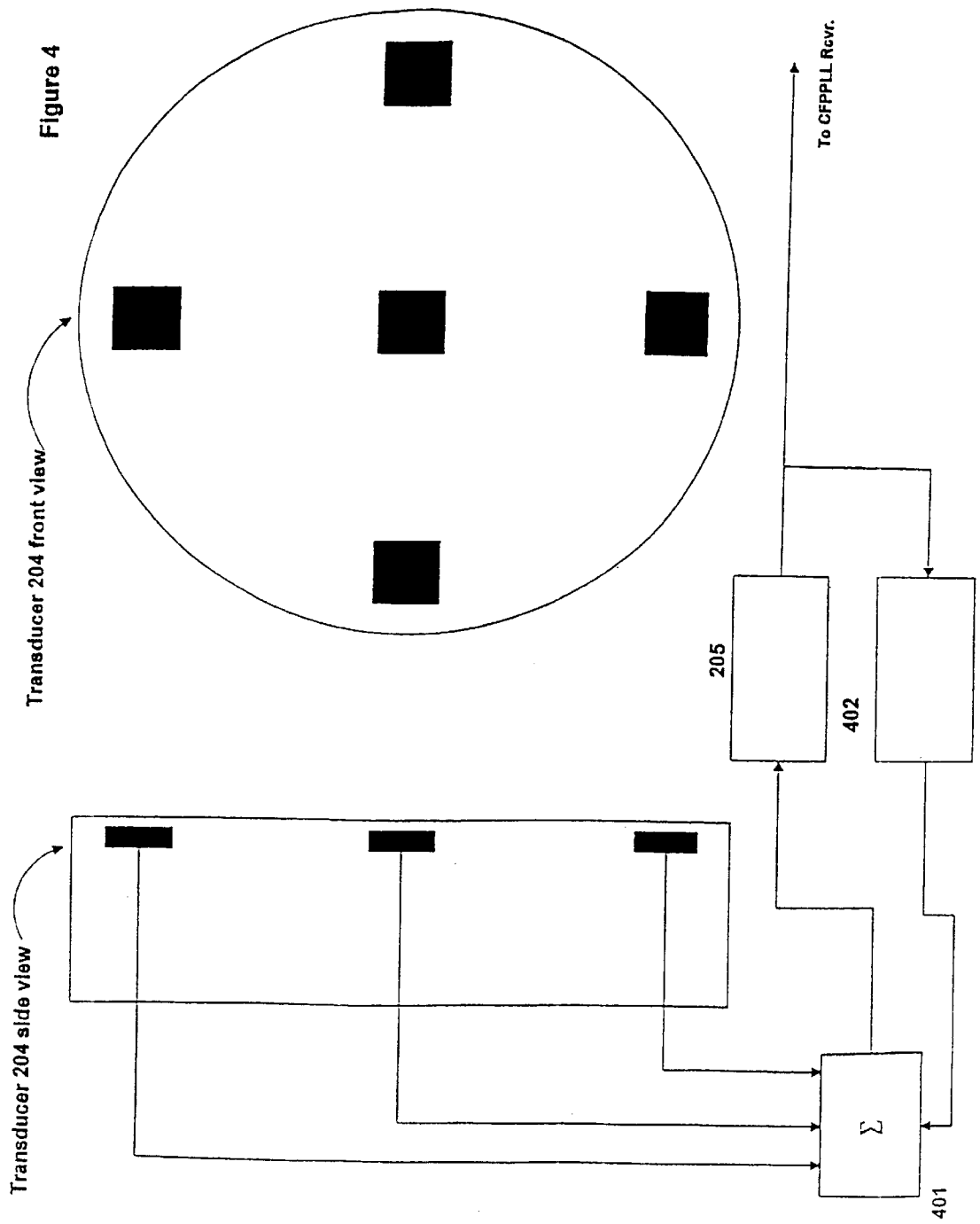
FIG. 4 is a schematic view showing a side view and a front view of one embodiment of a transducer (204).

It will be further understood by those of skill in the art that transducers A and B of FIG. 1a could be embodied as an essentially circular array of smaller transducers with the appropriate phase and amplitude weighting and summing circuits attached to each transducer, as shown in FIG. 4. In this embodiment, the servo alignment mechanism includes a system to determine the phase and amplitude of each channel in a receiver transducer. In this manner, electronic steering of the beam of each transducer array could be accomplished.

Front and side views of a typical transducer (204) are schematically depicted in FIG. 4, having an essentially circular array of five transducers. Although only three channels are shown in FIG. 4, it is understood that five are present. Each channel input is routed from the range discrimination gate (205) into the phase and amplitude adjustment apparatus (401), where phase and amplitude are automatically adjusted during the alignment procedure by the phase and amplitude computer (402). The resultant signal is then routed to the CFPPLL receiver as in the other embodiments.

Figure 5:
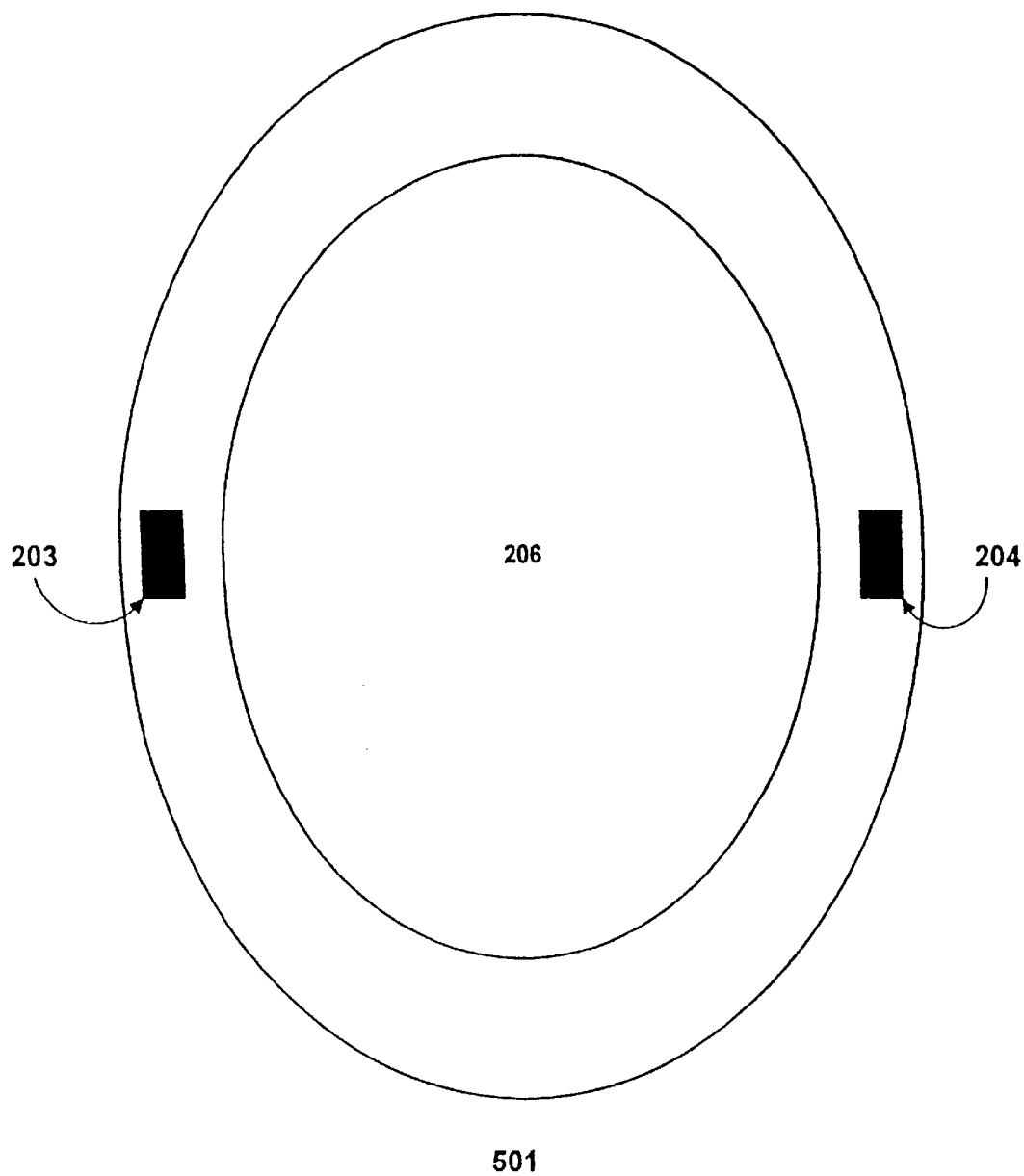
FIG. 5 shows still another embodiment in relation to patient (206), wherein transducer alignment can be accomplished by permanently aligning transducers (203) and (204) at the time of manufacture in a support helmet (501).

In still another embodiment, a fixed mechanical alignment could be accomplished by permanently aligning the transducers (203) and (204) at the time of manufacture in a support helmet (501) shown in FIG. 5 mounted on the target patient (206). In this embodiment, no further alignment is required.

It will be apparent to those skilled in the art that many other embodiments of the apparatus described hereinabove could be realized which would fall within the scope of the present invention.

We claim:

1. A method for monitoring changes in the intracranial pressure of humans and other vertebrates, comprising the steps of:

providing a first acoustic transducer and positioning said first transducer externally adjacent to the cranium of said human or other vertebrate;

providing a second acoustic transducer and positioning said second transducer externally adjacent to the cranium of said human or other vertebrate and diametrically opposed to said first transducer;

transmitting a first acoustic signal into the cranial vault of said human or other vertebrate from said first transducer towards said second transducer;

receiving a first reflected acoustic signal at said first transducer, said first reflected signal comprising at least a signal component indicative of a first wall of said cranial vault near said first transducer and a signal component indicative of a second wall of said cranial vault opposite said first transducer;

transmitting a second acoustic signal into the cranial vault of said human or other vertebrate from said second transducer towards said first transducer;

receiving a second reflected acoustic signal at said second transducer, said second reflected signal comprising at least a signal component indicative of said second wall of said cranial vault near said second transducer and a signal component indicative of said first wall of said cranial vault opposite said second transducer;

calculating a signal transit time across said cranial vault from said signal components indicative of said walls of said cranial vault;

determining from said calculated transit time a relative width of said cranial vault;

repeating said steps of transmitting and receiving said acoustic signals, calculating said transit time, and determining said relative width to identify changes in said relative width of said cranial vault; and associating changes in said relative width of said cranial vault with corresponding changes in said intracranial pressure.

2. An apparatus for monitoring changes in the intracranial pressure of humans and other vertebrates, comprising:

a first acoustic transducer positioned externally adjacent to the cranium of said human or other vertebrate, said first transducer transmitting an interrogating signal into the cranial vault of said human or vertebrate and receiving a reflected signal therefrom;

a second acoustic transducer positioned externally adjacent to the cranium of said human or other vertebrate and diametrically opposed to said first transducer, said second transducer transmitting an interrogating signal into the cranial vault of said human or vertebrate and receiving a reflected signal therefrom;

means for generating and transmitting a control signal to said acoustic transducers;

means for receiving and analyzing said reflected signals from said acoustic transducers;

means for alternately switching said control signal between said first transducer and said second transducer;

means for alternately switching said reflected signals between said first transducer and said second transducer;

means for discriminating a cranial vault transit time from said analyzed reflected signals; and means for identifying changes in said cranial vault transit time and correlating said transit time changes with changes in said intracranial pressure.

* * * * *